(12) United States Patent
Cole, Jr.

(10) Patent No.: US 11,883,690 B2
(45) Date of Patent: Jan. 30, 2024

(54) MULTI-DIRECTIONAL FILTRATION ARRANGEMENT, FLOW GENERATING DEVICE AND SYSTEM INCLUDING SAME

(71) Applicant: KONINKLIJKE PHILIPS N.V., Eindhoven (NL)

(72) Inventor: Kenneth E Cole, Jr., New Alexandria, PA (US)

(73) Assignee: Koninklijke Philips N.V., Eindhoven (NL)

( * ) Notice: Subject to any disclaimer, the term of this patent is extended or adjusted under 35 U.S.C. 154(b) by 523 days.

(21) Appl. No.: 17/021,309

(22) Filed: Sep. 15, 2020

(65) Prior Publication Data

US 2021/0128954 A1   May 6, 2021

Related U.S. Application Data

(60) Provisional application No. 62/929,988, filed on Nov. 4, 2019.

(51) Int. Cl.
*A62B 23/02* (2006.01)
*B01D 46/00* (2022.01)
*A62B 7/10* (2006.01)

(52) U.S. Cl.
CPC .............. *A62B 23/02* (2013.01); *A62B 7/10* (2013.01); *B01D 46/0005* (2013.01)

(58) Field of Classification Search
CPC ............ A61M 16/107; A61M 16/0057; A61M 16/0066; A61M 16/105; A61M 16/106; B01D 46/0005; B01D 2265/06; F04D 29/703; A62B 23/02; A62B 7/10
See application file for complete search history.

(56) References Cited

U.S. PATENT DOCUMENTS

| | | | |
|---|---|---|---|
| 3,951,625 A | * | 4/1976 | Follette ..................... F24F 3/14 261/80 |
| 4,226,234 A | | 10/1980 | Gunderson |
| 5,438,981 A | | 8/1995 | Devinney et al. |
| 10,238,822 B2 | | 3/2019 | Barlow et al. |

(Continued)

FOREIGN PATENT DOCUMENTS

WO   WO-2018104437 A1 * 6/2018 ........ A61M 16/0057

*Primary Examiner* — Joseph D. Boecker
*Assistant Examiner* — Brian T Khong
(74) *Attorney, Agent, or Firm* — Daniel H. Brean; Andrew M. Gabriel

(57) ABSTRACT

A filtration arrangement includes a filtration element and a housing disposed around, and retaining the filtration element therein. The housing includes: a first and second ends and a wall portion extending therebetween. An outlet is defined in the housing proximate the first end, a primary inlet is defined in the housing proximate the second end, and a plurality of secondary inlets are defined in the wall portion. The first end of the housing is adapted for coupling to a main housing of a flow generating device encircling an air inlet thereof. The primary and secondary inlets are positioned and structured to communicate ambient air from the surrounding environment to the filtration element. the outlet is positioned and structured to communicate the ambient air that has passed through the filtration element from one or more of the primary and secondary inlets to the air inlet of the flow generating device.

13 Claims, 6 Drawing Sheets

(56) References Cited

U.S. PATENT DOCUMENTS

2007/0163588 A1\* 7/2007 Hebrank ........... A61M 16/0069
128/205.29
2012/0167879 A1 7/2012 Becker et al.
2017/0165445 A1\* 6/2017 Zereshkian .............. A62B 7/10

\* cited by examiner

US 11,883,690 B2

MULTI-DIRECTIONAL FILTRATION ARRANGEMENT, FLOW GENERATING DEVICE AND SYSTEM INCLUDING SAME

CROSS-REFERENCE TO RELATED APPLICATIONS

This patent application claims the priority benefit under 35 U.S.C. § 119(e) of U.S. Provisional Application No. 62/929,988 filed on Nov. 4, 2019, the contents of which are herein incorporated by reference.

BACKGROUND OF THE INVENTION

1. Field of the Invention

The present invention generally relates to filtration arrangements and, more particularly, to multi-directional filtration arrangements for respiratory devices, such as ventilators or other pressure support systems. The present invention also relates to flow generating devices, such as ventilators or other pressure support systems, that include such filtration arrangements.

2. Description of the Related Art

Flow generating devices, such as ventilators and pressure support systems used in providing positive airway pressure therapies to a patient via a patient interface, draw air from the ambient environment and utilize such air in providing a flow of breathing gas to the airway of a patient. Such devices incorporate some form or forms of particulate and/or chemical filtration. Such filtration mitigates damage to the devices internal components and prevents foreign matter from entering the patient air path. Such inlet filters must be effective without inducing too high of an impedance in the flow path.

Air inlets of flow generating devices can become occluded, either passively or actively. Such occlusions can be partial or full. An occlusion can result from a respiratory device being physically placed in a space that could confine the air inlet (against a wall, adjacent a bed, etc.), or while operating the device could pull an object over the inlet area. Such occlusion could lead to a degradation in performance resulting in harm or even death to a patient receiving treatment from the respiratory device.

SUMMARY OF THE INVENTION

As one aspect of the present invention a filtration arrangement comprises: a filtration element; and a housing disposed around, and retaining the filtration element therein. The housing comprises: a first end, a second end opposite the first end, and a wall portion extending between the first end and the second end; an outlet defined in the housing proximate the first end; a primary inlet defined in the housing proximate the second end; and a plurality of secondary inlets defined in the wall portion, wherein the first end of the housing is structured to be coupled to a main housing of a flow generating device encircling an air inlet of the flow generating device, wherein the primary inlet and the secondary inlets are positioned and structured to communicate ambient air from the surrounding environment to the filtration element, and wherein the outlet is positioned and structured to communicate the ambient air that has passed through the filtration element from one or more of the primary inlet and secondary inlets to the air inlet of the flow generating device.

The primary inlet may be disposed generally in a first reference plane and at least one of the secondary inlets may be disposed generally in a second reference plane disposed at a non-zero angle with respect to the first reference plane.

The primary inlet may have a primary inlet area, wherein each of the secondary inlets have a secondary inlet area, wherein the primary inlet area is sized to be greater than or equal to a minimum area of the air inlet of the flow generating device, and wherein each of the secondary inlets are sized such that a combined area of all of the secondary inlet areas is greater than or equal to the minimum area of the air inlet of the flow generating device.

The outlet may be disposed in a third plane disposed parallel to the first plane.

The housing may be disc shaped and the primary inlet may be defined proximate a central portion of the housing and the plurality of secondary inlets may be disposed radially outward from the primary inlet.

The filtration element may be of a cylindrical shape. The filtration element may comprise an open cell urethane foam.

As another aspect of the invention a flow generating device for use in providing a flow of a breathing gas to an airway of a patient comprises: a main housing having an ambient air inlet and a breathing gas outlet defined therein; a flow generating arrangement disposed within the housing for producing the flow of breathing gas, the flow generating arrangement coupled between the air inlet and the breathing gas outlet and being structured to receive a flow of ambient air from the air inlet and provide the flow of breathing gas to the breathing gas outlet; and a filtration arrangement such as previously described.

As yet a further aspect of the present invention, a system for providing a flow of a breathing gas to an airway of a patient comprises: a patient interface structured to be engaged with the airway of the patient; and a flow generating device comprising: a main housing having an ambient air inlet and a breathing gas outlet defined therein, the outlet being coupled to the patient interface; a flow generating arrangement disposed within the housing for producing the flow of breathing gas, the flow generating arrangement coupled between the air inlet and the breathing gas outlet and being structured to receive a flow of ambient air from the air inlet and provide the flow of breathing gas to the breathing gas outlet and subsequently to the patient interface; and a filtration arrangement such as previously described.

These and other objects, features, and characteristics of the present invention, as well as the methods of operation and functions of the related elements of structure and the combination of parts and economies of manufacture, will become more apparent upon consideration of the following description and the appended claims with reference to the accompanying drawings, all of which form a part of this specification, wherein like reference numerals designate corresponding parts in the various figures. It is to be expressly understood, however, that the drawings are for the purpose of illustration and description only and are not intended as a definition of the limits of the invention.

DETAILED DESCRIPTION OF EXEMPLARY EMBODIMENTS

Figure 1:
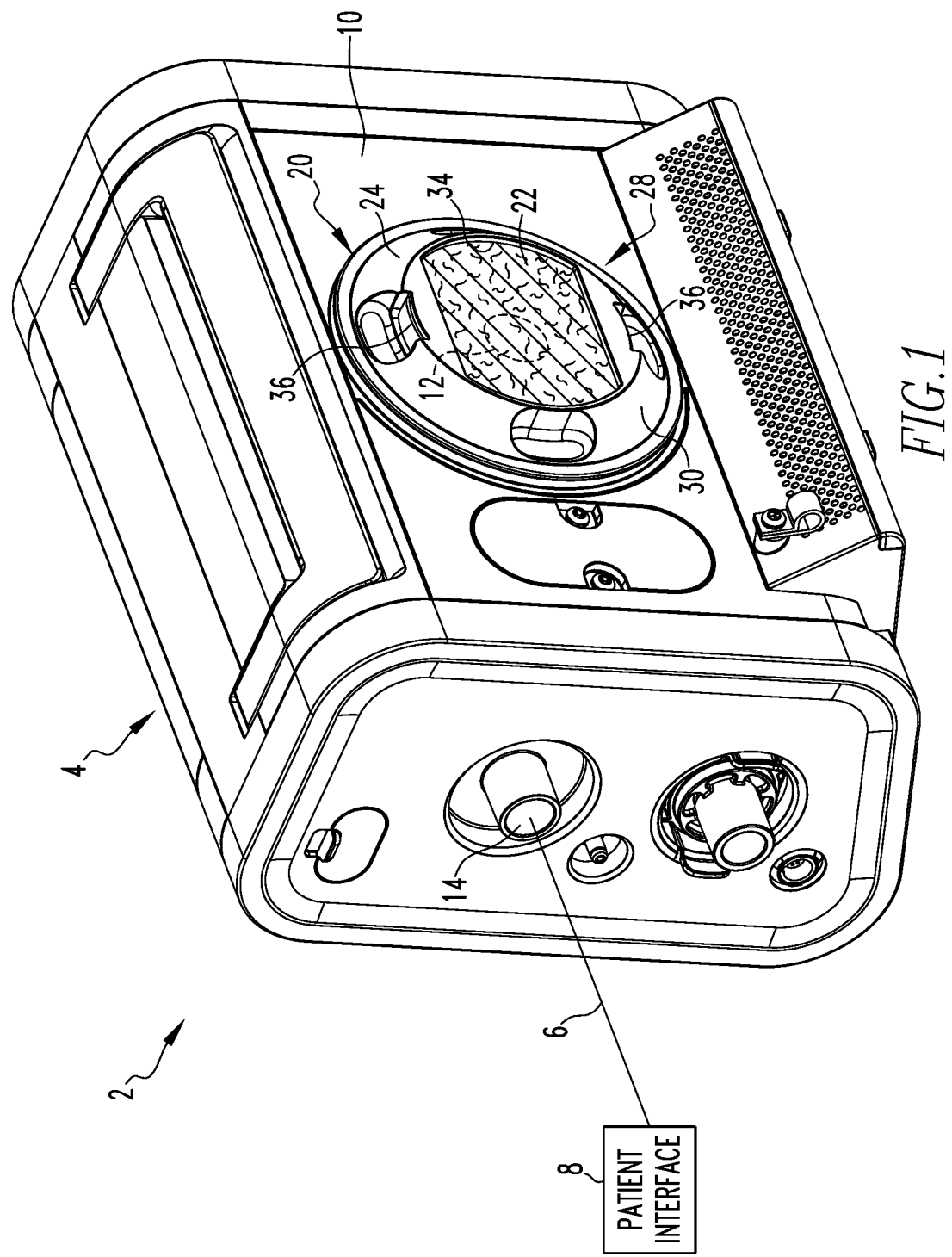
FIG. 1 is a partially schematic perspective view of a system adapted to provide a regimen of respiratory therapy to a patient including a flow generating device having a filtration arrangement according to one example embodiment of the present invention.

As used herein, the singular form of "a", "an", and "the" include plural references unless the context clearly dictates otherwise. As used herein, the statement that two or more parts or components are "coupled" shall mean that the parts are joined or operate together either directly or indirectly, i.e., through one or more intermediate parts or components, so long as a link occurs. As used herein, "directly coupled" means that two elements are directly in contact with each other. As used herein, "fixedly coupled" or "fixed" means that two components are coupled so as to move as one while maintaining a constant orientation relative to each other.

As used herein, the statement that two or more parts or components "engage" one another shall mean that the parts exert a force against one another either directly or through one or more intermediate parts or components. As employed herein, the term "number" shall mean one or an integer greater than one (i.e., a plurality). Directional phrases used herein, such as, for example and without limitation, left, right, upper, lower, front, back, on top of, and derivatives thereof, relate to the orientation of the elements shown in the drawings and are not limiting upon the claims unless expressly recited therein. As employed herein, the term "and/or" shall mean one or both of the elements separated by such term. For example, "A and/or B" would mean any of: i) A, ii) B, or iii) A and B.

A system 2 for providing a flow of breathing gas to an airway of a patient according to one exemplary embodiment of the invention is generally shown in FIG. 1. System 2 includes a flow generating device 4, a delivery conduit 6 (shown schematically), and a patient interface 8 (also shown schematically). Flow generating device 4 is structured to generate a flow of breathing gas and may include, without limitation, ventilators, constant pressure support devices (such as a continuous positive airway pressure device, or CPAP device), variable pressure devices (e.g., BiPAP®, Bi-Flex®, or C-Flex™ devices manufactured and distributed by Philips Respironics of Murrysville, Pennsylvania), and auto-titration pressure support devices. Delivery conduit 6 is structured to communicate the flow of breathing gas from flow generating device 4 to patient interface 8.

A BiPAP® device is a bi-level device in which the pressure provided to the patient varies with the patient's respiratory cycle, so that a higher pressure is delivered during inspiration than during expiration. An auto-titration pressure support system is a system in which the pressure varies with the condition of the patient, such as whether the patient is snoring or experiencing an apnea or hypopnea. For present purposes, flow/flow generating device 4 is also referred to as a gas flow generating device, because flow results when a pressure gradient is generated. The present invention contemplates that flow generating device 4 is any conventional system for delivering a flow of gas to an airway of a patient or for elevating a pressure of gas at an airway of the patient, including the pressure support systems summarized above and non-invasive ventilation systems.

Patient interface 8 may be any suitable interface device used for interfacing any of the flow generating devices previously described with an airway of a patient.

Figure 2:
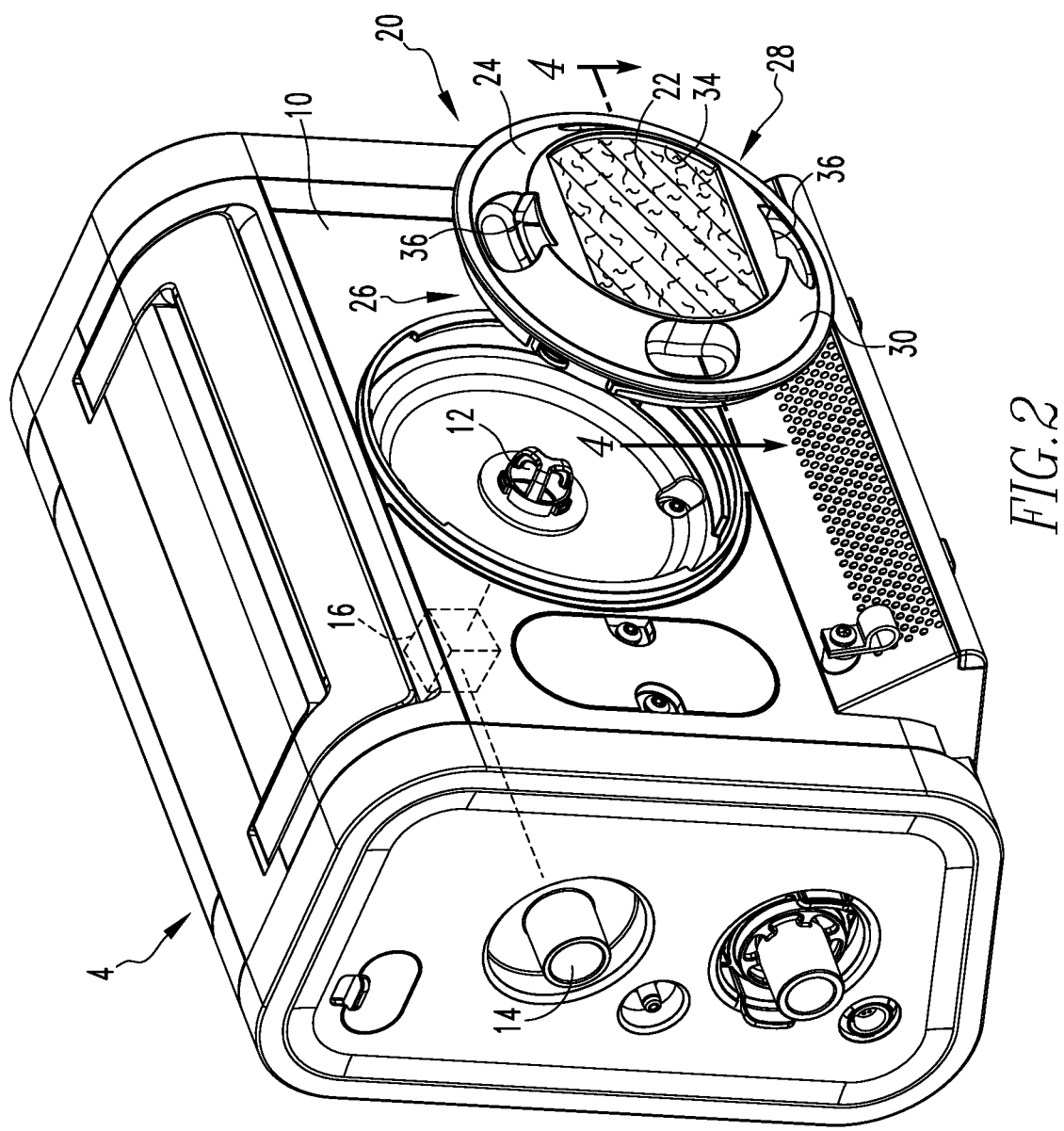
FIG. 2 is a perspective view of the flow generating device of FIG. 1 shown with the filtration arrangement exploded therefrom.
Figure 3:
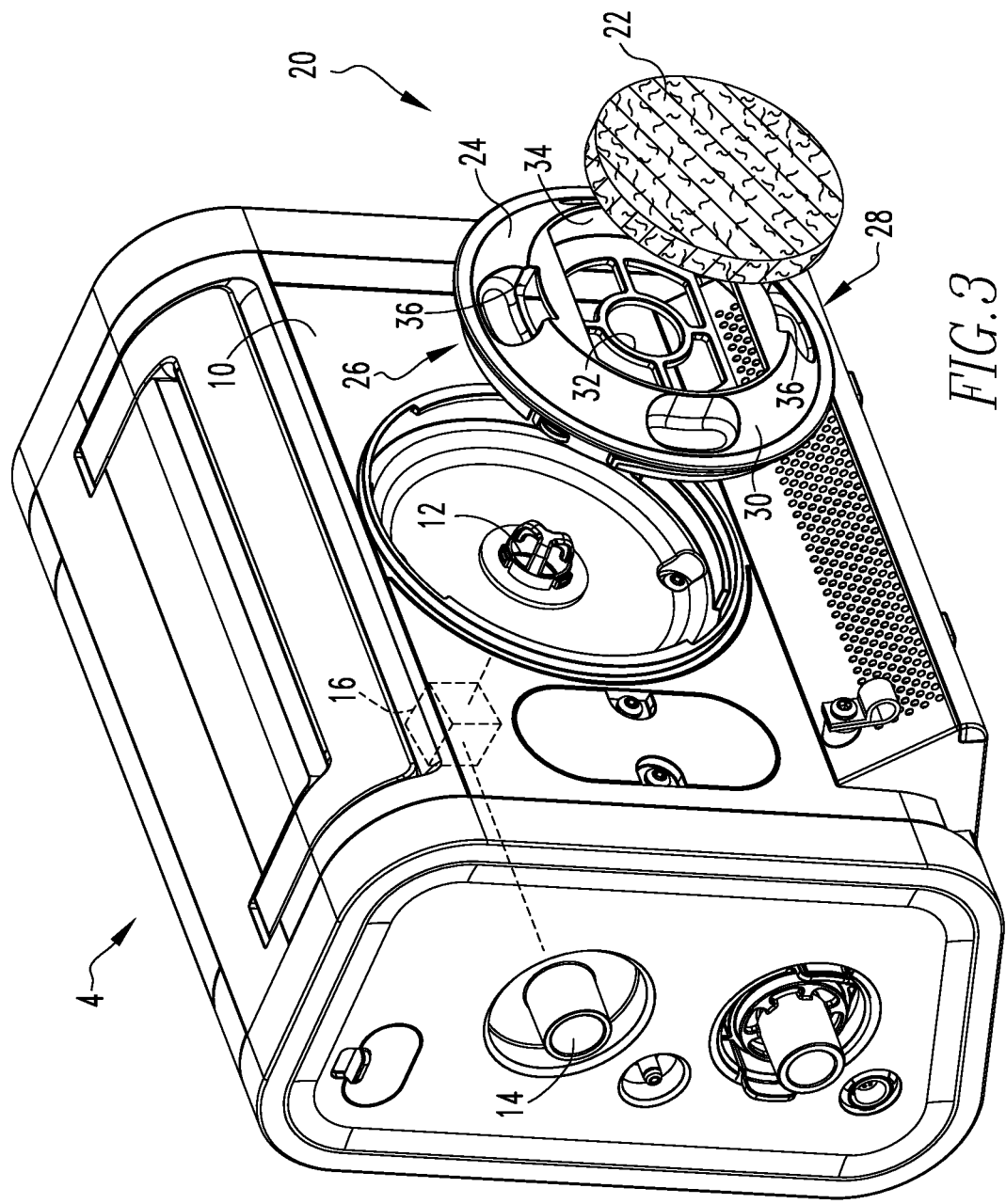
FIG. 3 is a perspective view of the flow generating device of FIG. 2 shown with the filtration arrangement exploded showing a housing and filtration element thereof according to one example embodiment of the present invention.

Continuing to refer to FIG. 1, as well as to FIGS. 2 and 3, flow generating device 4 includes a main housing 10 having an ambient air inlet 12 and a breathing gas outlet 14 defined therein. Main housing 10 may be formed from a plurality of separate elements that may be selectively or permanently coupled together. Breathing gas outlet 14 is structured to be coupled to patient interface 8 via conduit 6. Flow generating device 4 further includes a flow generating arrangement 16 (shown schematically in hidden line in FIGS. 2 and 3) coupled between air inlet 12 and breathing gas outlet 14. Flow generating arrangement 16 is structured to receive a flow of ambient air from air inlet 12 and provide the flow of breathing gas to breathing gas outlet 14 (which is subsequently passed on to the patient via conduit 6 and patient interface 8).

In order to prevent unwanted particulates from being sucked into flow generating arrangement 16 during operation, flow generating device 4 further includes a filtration arrangement 20 covering air inlet 12 that is selectively coupled to main housing 10. Filtration arrangement 20 includes a filtration element 22 and a housing 24 that is generally disposed around, and retains filtration element 22 therein. Filtration element 22 is formed from a suitable filtration medium such as an open cell urethane foam or any other suitable material for use in filtering small particles from the ambient air. In In the example shown in the FIGS. filtration element 22 is cylindrically shaped (e.g., see FIG. 3), however, it is to be appreciated that filtration element 22 may generally be of any shape without varying from the scope of the present invention.

Figure 4:
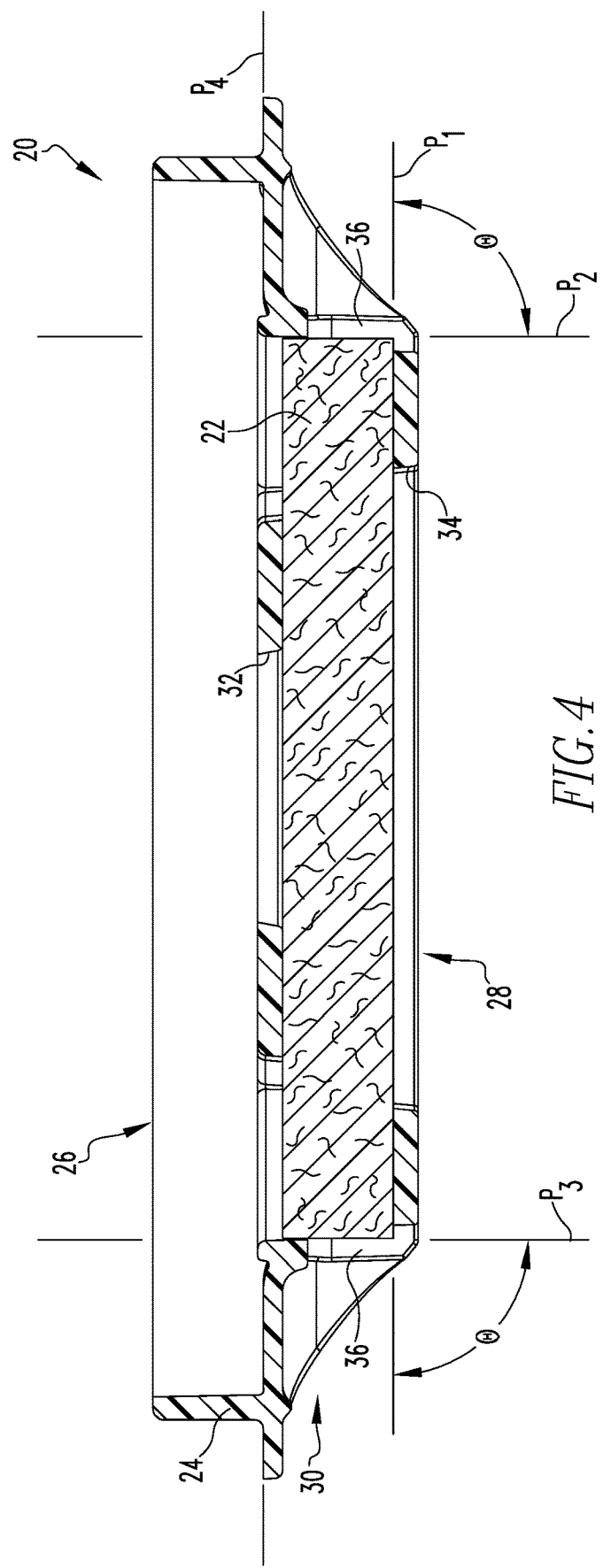
FIG. 4 is an elevation section view of the filtration arrangement taken along line 4-4 of FIG. 2.
Figure 5A:
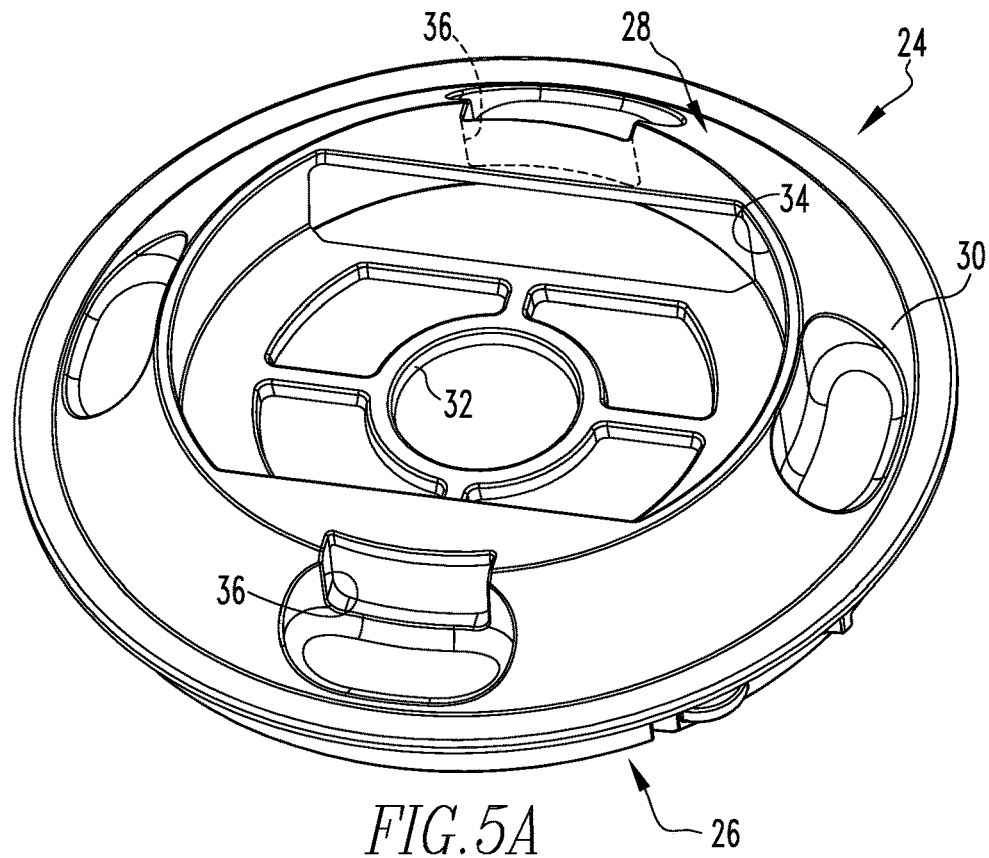
FIGS. 5A and 5B show perspective views of the housing of the filtration arrangement of FIGS. 1-3.
Figure 5B:
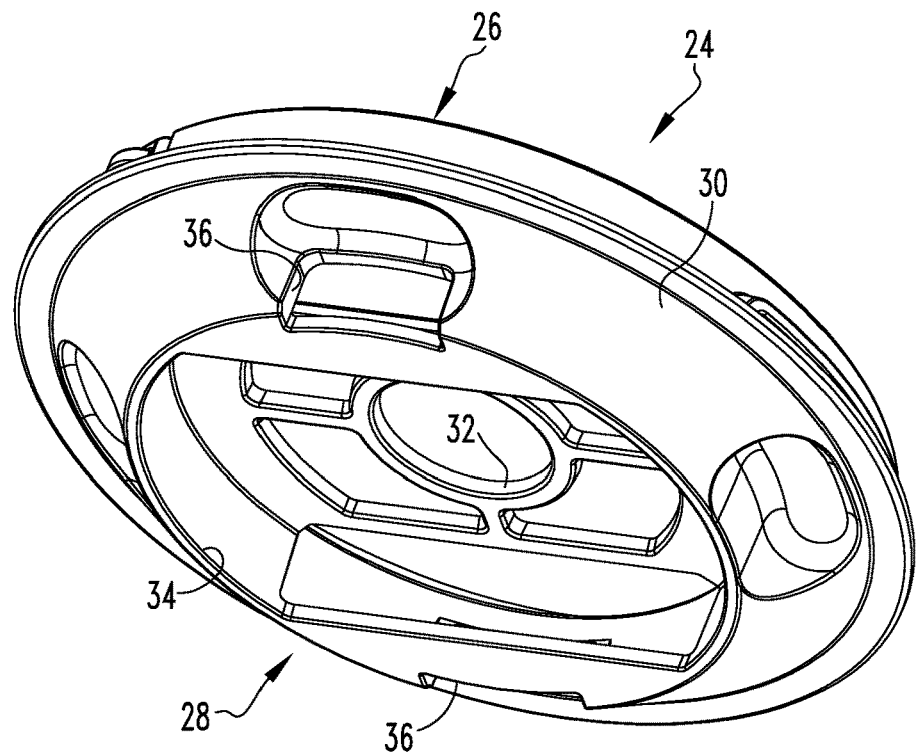

Referring now to FIGS. 4, 5A and 5B, in addition to FIGS. 1-3, housing 24 includes a first end 26, a second end 28 opposite first end 26, and a wall portion 30 that extends between first end 26 and second end 28. First end 26 is selectively coupled to main housing 10 generally encircling air inlet 12. In the one example shown in the FIGS., first end 26 is selectively coupled to main housing 10 via a threaded arrangement such that housing 24 (and thus filtration arrangement 20) may readily be uncoupled or recoupled to main housing 10 via rotation of housing 24 of filtration arrangement 20 generally about the central axis thereof in one of a first or a second direction, however, it is to be appreciated that other selective coupling arrangements (e.g., snap-fit, friction fit, etc.) may be employed without varying from the scope of the present invention. An outlet 32 is defined in housing 24 proximate first end 26. A primary inlet 34 is defined in housing 24 proximate second end 28. A plurality of secondary inlets 36 are defined in wall portion 30. The example housing 24 shown in the FIGS. includes two secondary inlets 36 spaced 180° about the center of housing 24, however, it is to be appreciated that one or more of the quantity and/or spacing of secondary inlets 36 may be varied without varying from the scope of the present invention. Primary inlet 34 and secondary inlets 36 are positioned and structured to communicate all or portions of the flow of the ambient air from the surrounding environment to filtration element 22, while outlet 32 is positioned and structured to communicate the flow of ambient air from filtration element 22 to air inlet 12 of flow generating device 4. In the one example embodiment shown in the FIGS., housing 24 is generally disc-shaped and primary inlet 34 is defined proximate a central portion of housing 24 while secondary inlets 36 are disposed radially outward from primary inlet 34, however, it is to be appreciated that housing 24 main be of other shape and/or dimensions and that primary and secondary inlets 34 and 36 may be arranged in different positionings without varying from the scope of the present invention. It is also to be appreciated that although shown as each being single apertures, one or more of primary inlet 34 and secondary inlets 36 may be subdivided by portions of housing 24 or via one or more other elements without varying from the scope of the present invention.

Referring now to FIG. 4, primary inlet 34 is disposed generally in a first reference plane P1, while each of secondary inlets 36 are disposed respectively in a second plane P2 and a third plane P3 that are each angled at an angle θ, φ with respect to first plane P. As used herein, the term "angled" shall refer to two elements that are positioned such that they do not lie in the same plane, and thus form an angle therebetween that is not zero, 180° or a multiple thereof. In the example shown in FIG. 4, each of secondary inlets 36 are generally disposed, respectively, in first and second reference planes P2 and P3 oriented at about 90° with respect to first reference plane P1, however, it is to be appreciated that other values of angles θ and φ (aside from zero, 180° and multiples thereof) may be employed without varying from the scope of the present invention. Also in the example shown in FIG. 4, outlet 32 is disposed in a fourth reference plane P4 disposed generally parallel to reference plane P1, however, it is to be appreciated that outlet 32 and primary inlet 34 may be disposed in a non-parallel relationship without varying from the scope of the present invention. It is thus to be appreciated that such arrangement of primary and secondary inlets 34 and 36 provides for air inlet and filtration thereof in multiple directions disassociated from primary inlet 34, thus if primary inlet 34 becomes occluded, filtered air is still available via secondary inlets 36 and thus therapy can still be provided with no disruption.

Figure 6:
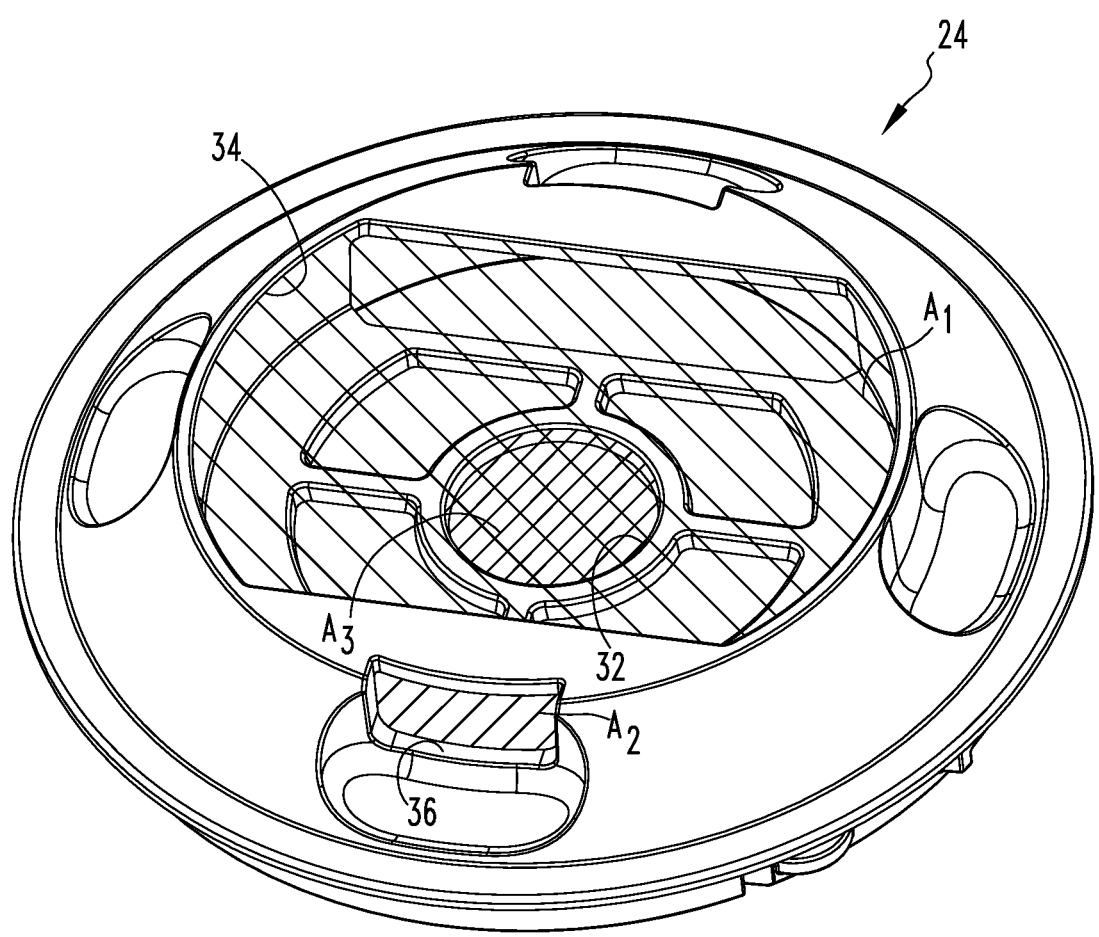
FIG. 6 is a perspective view of the housing of the filtration arrangement of FIGS. 1-3 similar to FIG. 5A but having hatched areas showing areas defined buy different portions of the housing.

In order to prevent degradation in performance of flow generating device 4 if primary inlet 34 becomes occluded, the total area of all of secondary inlets 36 is equal to, or greater than, a minimum area of air inlet 12 of flow generating device 4 (as is the area of primary inlet 34). FIG. 6 shows with cross-hatching the general areas defined by primary inlet 34, secondary inlets 36, and outlet 32 (which in the one example embodiment shown is sized generally the same as the minimum area of inlet 12). Accordingly, FIG. 6 shows: a primary inlet area A1 that is defined by primary inlet 34, a secondary inlet area A2 that is defined by one of secondary inlets 36, and outlet area A3 (that in the example shown in FIG. 6 is sized generally the same as the minimum area of inlet 12 of flow generating device 4).

In the claims, any reference signs placed between parentheses shall not be construed as limiting the claim. The word "comprising" or "including" does not exclude the presence of elements or steps other than those listed in a claim. In a device claim enumerating several means, several of these means may be embodied by one and the same item of hardware. The word "a" or "an" preceding an element does not exclude the presence of a plurality of such elements. In any device claim enumerating several means, several of these means may be embodied by one and the same item of hardware. The mere fact that certain elements are recited in mutually different dependent claims does not indicate that these elements cannot be used in combination.

Although the invention has been described in detail for the purpose of illustration based on what is currently considered to be the most practical and preferred embodiments, it is to be understood that such detail is solely for that purpose and that the invention is not limited to the disclosed embodiments, but, on the contrary, is intended to cover modifications and equivalent arrangements that are within the spirit and scope of the appended claims. For example, it is to be understood that the present invention contemplates that, to the extent possible, one or more features of any embodiment can be combined with one or more features of any other embodiment.

What is claimed is:

1. A filtration arrangement comprising:
   a filtration element; and
   a housing disposed around, and retaining the filtration element therein, the housing comprising:
      a first end, a second end opposite the first end, and a wall portion comprising a first surface extending between the first end and the second end and a second surface extending between the first end and the second end, wherein the first and second surfaces are not coplanar;
      an outlet defined in the housing proximate the first end;
      a primary inlet defined in the housing proximate the second end; and
      a plurality of secondary inlets each defined by an opening in both of the first and second surfaces of the wall portion,
      wherein the second surface is annular and wherein each of the secondary inlets extends in a circumferential direction greater than in a lateral direction,
   wherein the first end of the housing is structured to be coupled to a main housing of a flow generating device encircling an air inlet of the flow generating device,
   wherein the primary inlet and the secondary inlets are positioned and structured to communicate ambient air from a surrounding environment to the filtration element,
   wherein the outlet is positioned and structured to communicate the ambient air that has passed through the filtration element from one or more of the primary inlet and secondary inlets to the air inlet of the flow generating device, and
   wherein the primary inlet has a primary inlet area, wherein each of the secondary inlets have a secondary inlet area, wherein the primary inlet area is sized to be greater than or equal to a minimum area of the air inlet of the flow generating device, and wherein each of the secondary inlets are sized such that a combined area of all of the secondary inlet areas is greater than or equal to the minimum area of the air inlet of the flow generating device.

2. The filtration arrangement of claim 1, wherein the primary inlet is disposed generally in a first reference plane and wherein at least one of the secondary inlets is disposed in the second surface of the wall portion surrounding the filtration element generally in a second reference plane disposed at a non-zero angle with respect to the first reference plane.

3. The filtration arrangement of claim 2, wherein the outlet is disposed in a third reference plane disposed parallel to the first reference plane.

4. The filtration arrangement of claim 1, wherein the housing is disc shaped and wherein the primary inlet is defined proximate a central portion of the housing and wherein the plurality of secondary inlets are disposed radially outward from the primary inlet in the second surface of the wall portion surrounding the filtration element at 180 degrees from one another.

5. The filtration arrangement of claim 1, wherein the filtration element is of a cylindrical shape.

6. The filtration arrangement of claim 1, wherein the opening in both of the first surface and the second surface of the wall portion comprise openings in respective ones of the first and second surface that are aligned to form the plurality of secondary inlets.

7. A flow generating device for use in providing a flow of a breathing gas to an airway of a patient, the flow generating device comprising:
  a main housing having an ambient air inlet and a breathing gas outlet defined therein;
  a flow generating arrangement disposed within the main housing for producing the flow of breathing gas, the flow generating arrangement coupled between the ambient air inlet and the breathing gas outlet and being structured to receive a flow of ambient air from the ambient air inlet and provide the flow of breathing gas to the breathing gas outlet; and
  a filtration arrangement comprising:
    a filtration element; and
    a housing disposed around, and retaining the filtration element therein, the housing comprising:
      a first end, a second end opposite the first end, and a wall portion comprising a first surface extending between the first end and the second end and a second surface extending between the first end and the second end, wherein the first and second surfaces are not coplanar;
      an outlet defined in the housing proximate the first end:
      a primary inlet defined in the housing proximate the second end; and
      a plurality of secondary inlets defined by an opening in both of the first and second surfaces of the wall portion,
    wherein the second surface is annular and wherein each of the secondary inlets extends in a circumferential direction greater than in a lateral direction,
    wherein the first end of the housing is coupled to the main housing encircling the ambient air inlet,
    wherein the primary inlet and the secondary inlets are positioned and structured to communicate all or portions of the flow of the ambient air from a surrounding environment to the filtration element,
    wherein the outlet is positioned and structured to communicate the flow of the ambient air that has passed through the filtration element from one or more of the primary inlet and secondary inlets to the ambient air inlet of the flow generating device, and
    wherein the primary inlet has a primary inlet area, wherein each of the secondary inlets have a secondary inlet area, wherein the outlet has an outlet area, wherein the primary inlet area is greater than or equal to the outlet area, and wherein a combined area of all of the secondary inlet areas is greater than or equal to the outlet area.

8. The flow generating device of claim 7, wherein the primary inlet is disposed generally in a first plane and wherein at least one of the secondary inlets is disposed in the second surface of the wall portion surrounding the filtration element generally in a second plane angled with respect to the first plane.

9. The flow generating device of claim 8, wherein the outlet is disposed in a third plane disposed parallel to the first plane.

10. The flow generating device of claim 7, wherein the filtration element is of a cylindrical shape and comprises an open cell urethane foam.

11. The flow generating device of claim 7, wherein the housing of the filtration arrangement is disposed about a central axis and the primary inlet is defined proximate a central portion of the housing, and wherein the plurality of secondary inlets are disposed radially outward from the primary inlet in the second surface of the wall portion at 180 degrees from one another.

12. A system for providing a flow of a breathing gas to an airway of a patient, the system comprising:
  a patient interface structured to be engaged with the airway of the patient; and
  a flow generating device comprising:
  a main housing having an ambient air inlet and a breathing gas outlet defined therein, the breathing gas outlet being coupled to the patient interface;
  a flow generating arrangement disposed within the housing for producing the flow of breathing gas, the flow generating arrangement coupled between the ambient air inlet and the breathing gas outlet and being structured to receive a flow of ambient air from the ambient air inlet and provide the flow of breathing gas to the breathing gas outlet and subsequently to the patient interface; and
  a filtration arrangement comprising:
    a filtration element; and
    a housing disposed around, and retaining the filtration element therein, the housing comprising:
      a first end, a second end opposite the first end, and a wall portion comprising a first surface extending between the first end and the second end and a second surface extending between the first end and the second end, wherein the first and second surfaces are not coplanar;
      an outlet defined in the housing proximate the first end;
      a primary inlet defined in the housing proximate the second end; and
      a plurality of secondary inlets defined by an opening in both of the first and second surfaces of the wall portion,
    wherein the second surface is annular and wherein each of the secondary inlets extends in a circumferential direction greater than in a lateral direction,
    wherein the first end of the housing is coupled to the main housing encircling the ambient air inlet,
    wherein the primary inlet and the secondary inlets are positioned and structured to communicate all or portions of the flow of the ambient air from the surrounding environment to the filtration element,
    wherein the outlet is positioned and structured to communicate the flow of ambient air that has passed through the filtration element from one or more of the primary inlet and secondary inlets to the ambient air inlet of the flow generating device, and
    wherein the primary inlet has a primary inlet area, wherein each of the secondary inlets have a secondary inlet area, wherein the outlet has an outlet area, wherein the primary inlet area is greater than or equal to the outlet area, and wherein a combined area of all of the secondary inlet areas is greater than or equal to the outlet area.

13. The system of claim 12, wherein the primary inlet is disposed generally in a first reference plane and wherein at least one of the secondary inlets is disposed in the second surface generally in a second reference plane disposed at a non-zero angle with respect to the reference first plane, and wherein the plurality of secondary inlets are disposed radially outward from the primary inlet in the second surface of the wall portion at 180 degrees from one another.

* * * * *